(12) United States Patent
Groll et al.

(10) Patent No.: US 10,814,085 B1
(45) Date of Patent: Oct. 27, 2020

(54) AIRTIGHT MASK SEAL

(71) Applicant: Circadiance, LLC, Turtle Creek, PA (US)

(72) Inventors: David Groll, Murrysville, PA (US); Nadine Scandinaro, Export, PA (US); Alexander C. De Poix, Penn Hills, PA (US)

(73) Assignee: Circadiance LLC, Turtle Creek, PA (US)

( * ) Notice: Subject to any disclaimer, the term of this patent is extended or adjusted under 35 U.S.C. 154(b) by 509 days.

(21) Appl. No.: 15/828,378

(22) Filed: Nov. 30, 2017

Related U.S. Application Data

(60) Provisional application No. 62/428,321, filed on Nov. 30, 2016.

(51) Int. Cl.
*A61M 16/06* (2006.01)

(52) U.S. Cl.
CPC .... *A61M 16/0605* (2014.02); *A61M 16/0683* (2013.01)

(58) Field of Classification Search
CPC .............. A61M 16/06; A61M 16/0605; A61M 16/0616; A41D 13/11; A62B 7/00; A62B 7/10; A62B 23/02; A62B 23/025
See application file for complete search history.

(56) References Cited

U.S. PATENT DOCUMENTS

| | | | | |
|---|---|---|---|---|
| 1,946,334 | A | * | 2/1934 | Schwartz ............... A41D 13/11 128/206.16 |
| 2,775,967 | A | * | 1/1957 | Sovinsky ............. A62B 23/025 128/206.12 |
| 2009/0139525 | A1 | * | 6/2009 | Schirm ............. A61M 16/0605 128/205.25 |
| 2010/0006101 | A1 | * | 1/2010 | McAuley .......... A61M 16/0683 128/206.24 |
| 2011/0253144 | A1 | * | 10/2011 | Groll ................... A61M 16/125 128/206.24 |
| 2013/0192601 | A1 | * | 8/2013 | Reischl ............. A61M 16/0616 128/205.25 |
| 2014/0158136 | A1 | * | 6/2014 | Romagnoli ....... A61M 16/0875 128/206.24 |
| 2016/0213872 | A1 | * | 7/2016 | Paulk ................ A61M 16/0875 |
| 2017/0326320 | A1 | * | 11/2017 | Baigent ............ A61M 16/0683 |

* cited by examiner

*Primary Examiner* — Kathryn E Ditmer
(74) *Attorney, Agent, or Firm* — Metz Lewis Brodman Must O'Keefe LLC

(57) ABSTRACT

A mask for use in delivering air at a therapeutic pressure to a patient in need of therapy receives air from an air tube into an inelastic cloth mask portion that is attached to an interface portion constructed of an elastic material. The interface portion is a three dimensional structure that is attached at its edges to the mask portion and has a nose hole for receiving the patient's nose. When air is delivered the elastic interface portion pillows out and forms a seal against the patient's face. To assist with the seal, a structural assistance member may optionally be disposed on the interface portion above the nose hole so that it can be adjusted in the area of the bridge of the patient's nose.

14 Claims, 3 Drawing Sheets

AIRTIGHT MASK SEAL

CROSS-REFERENCE TO RELATED APPLICATIONS

This application claims the benefit of U.S. Provisional Patent Application Ser. No. 62/428,321, filed on Nov. 30, 2016, entitled "Airtight Mask Seal," the entirety of which is incorporated by reference as if more fully set forth herein.

FIELD OF THE INVENTION

The present invention relates to continuous positive airway pressure devices. More specifically, the present invention relates to methods and devices for providing a good seal for an all cloth mask to the user's face.

BACKGROUND OF THE INVENTION

Continuous positive airway pressure (CPAP) is a treatment for sleep apnea that uses elevated air pressure to keep a patient's airways shunted open. The treatment involves the use of a mask that covers the user's nasal, and occasionally oral, passages. The mask may be made of plastic or cloth materials. While current cloth masks provide more comfort than plastic masks, it is possible that air can still leak through the seal between the patient's face and the mask, which can cause many undesired side effects such as skin irritation, noise, or reduced therapeutic pressure, for example.

The problem of air leakage is compounded by the fact that mask fit flexibility must be maintained to ensure that nasal and oral mask chambers remain stable and in the proper positions. The enormous variability in patient nose shapes, mouth shapes, and facial hair make it extremely difficult to properly fit all patients with a few different standard sizes. Further, some nasal pillows and masks have protrusions that extend into the nasal passageways of the patient, which causes discomfort and additional maintenance and cleaning. It is therefore an object of the present invention to provide a CPAP mask that delivers improved sealing and comfort.

In addition to the various objects and advantages of the present invention which have been described above, various other objects and advantages of the invention will become more readily apparent to those persons skilled in the relevant art from the following more detailed description of the invention, particularly, when such description is taken in conjunction with the attached drawing figures and with the appended claims.

SUMMARY OF THE INVENTION

This summary is provided to comply with 37 C.F.R. § 1.73, requiring a summary of the invention briefly indicating the nature and substance of the invention. It is submitted with the understanding that it will not be used to interpret or limit the scope or meaning of the claims.

A mask assembly for delivering air at a therapeutic pressure from an air tube to a patient's air passages is provided and is intended to be used with headgear for keeping it on the patient's head. The mask assembly comprises a cloth mask portion having a proximal end and a distal end. The distal end is removably attached to the air tube in order to receive air into the mask. The mask assembly also comprises an elastic interface portion disposed on the proximal end of the cloth mask portion wherein air at therapeutic pressure inflates and expands the elastic interface portion to sealingly deliver the air to the patient's air passages.

In certain embodiments, the cloth mask portion is constructed of an inelastic material such as a cloth and the elastic interface portion is constructed from a material that is stretchable by over one hundred percent. In embodiments, the elastic interface portion is constructed from a single piece of material, but when constructed is creates a three dimensional structure. In embodiments, the three dimensional structure comprises one or more pleats formed in an outer edge. The outer edge is then disposed on the cloth mask portion by sewing, welding, bonding, gluing, or other means known in the art.

In certain embodiments, the interface portion is created from material cut into a specific shape having a first edge and a second edge that are pulled together and affixed to each other to create a three dimensional structure having a nose hole for receiving the patient's nose. Upon inflation, the interface portion expands and pushes against the patient's face to create a seal.

In embodiments, a structural assistance member is placed adjacent to the nose hole or above it in the area that would touch the bridge of the patient's nose when in use. The member either encircles the nose hole or one of chevron, rectangle, triangle or arc shaped. In further embodiments, the member is comprised of a material that is stiffer than the interface material. In certain embodiments, the structural assistance member is constructed of thin aluminum or thin plastic.

BRIEF DESCRIPTION OF THE DRAWINGS

The accompanying drawings, which are incorporated in and form a part of the specification, illustrate the embodiments of the invention and together with the written description serve to explain the principles, characteristics, and features of the invention. In the drawings.

DETAILED DESCRIPTION OF THE INVENTION

This disclosure describes examples of a pillowing seal structure for a mask and methods of producing the same. In the following description, for purposes of explanation, numerous specific details are set forth in order to provide a thorough understanding of certain embodiments. It will be evident to one skilled in the art, however, that embodiments can be practiced without these specific details.

Figure 1:
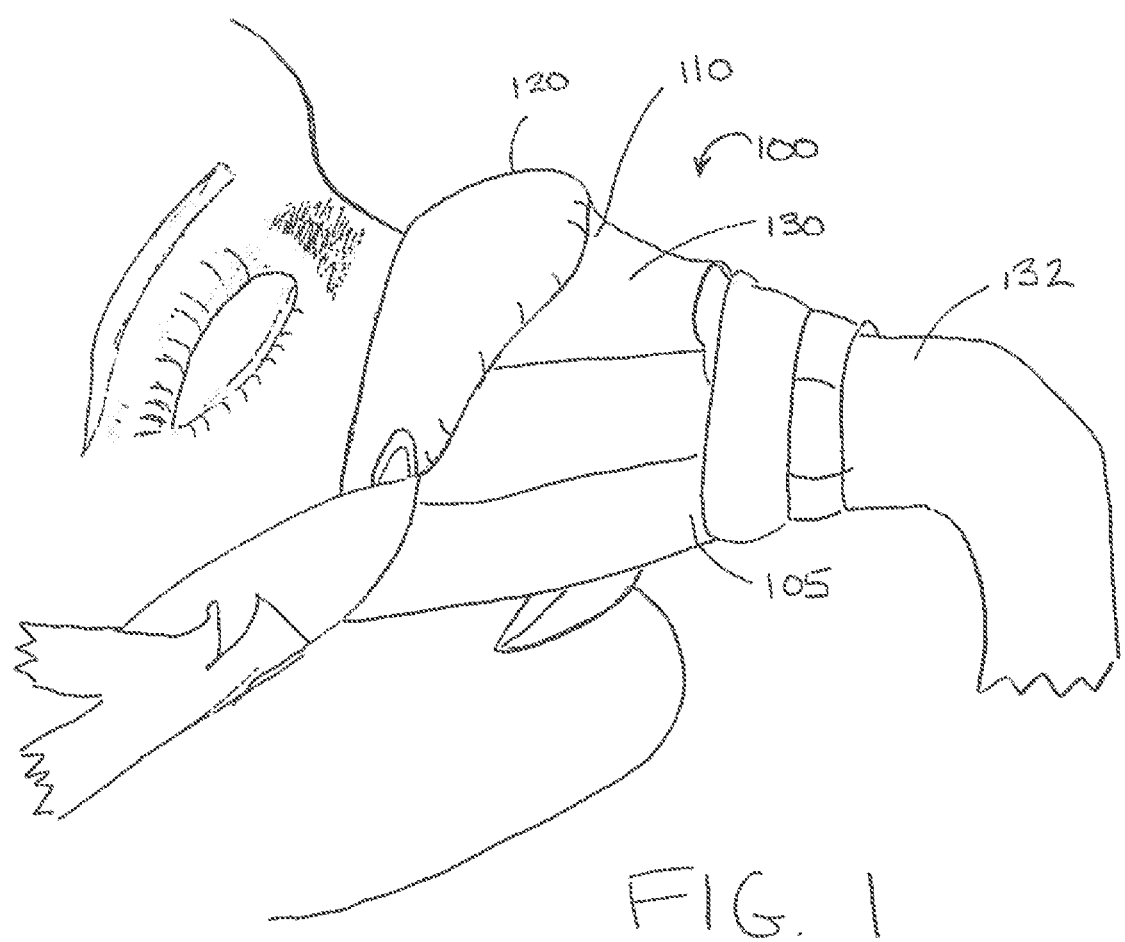
FIG. 1 is a perspective illustration of a CPAP mask having an airtight seal consistent with an embodiment of the invention.

FIG. 1 illustrates an embodiment of a non-rigid cloth frameless mask assembly 100 that can be used for CPAP therapy. Generally, cloth masks are known previously. See, for example, patent application Ser. No. 12/070,463 filed by Circadiance, LLC of Pittsburgh, Pa. The interface portion 120 is new. Due to its construction, the interface portion is designed to pillow between the patient's face and the proximal end 110 of the mask portion 130, thus enabling a better seal than was heretofore possible. The distal end 105 of the mask is removably attached to an air tube 132 that provides air to the mask portion 130 at a therapeutic pressure.

Figure 2:
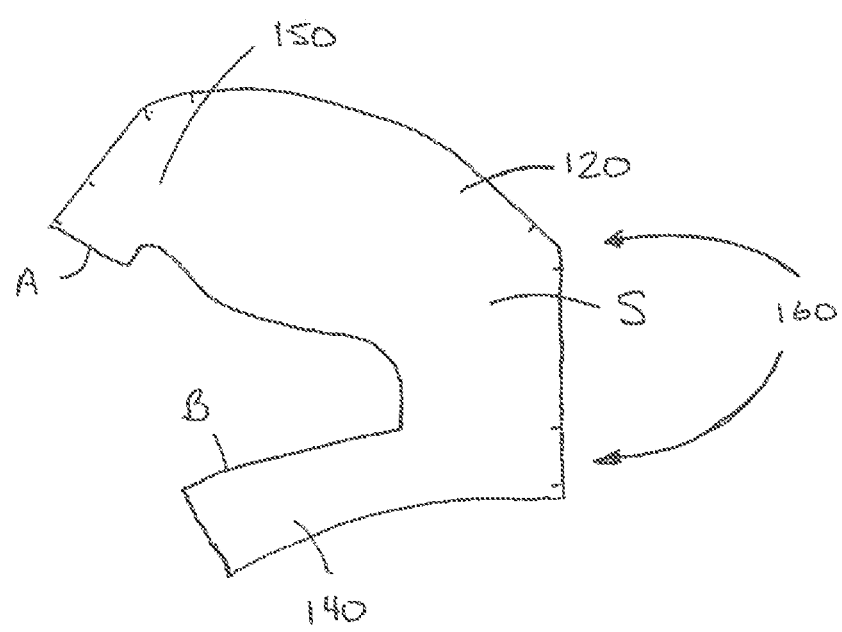
FIG. 2 is a plan view of a cutout pattern used to make the sealing interface of the present invention.
Figure 3:
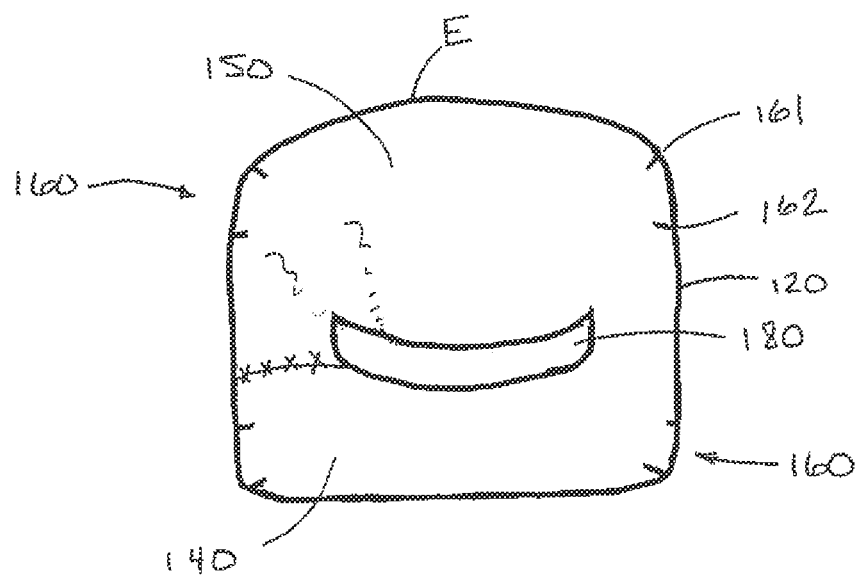
FIG. 3 is an elevational front view of an outside surface of a sealing interface prior to the addition of pleats.
Figure 4:
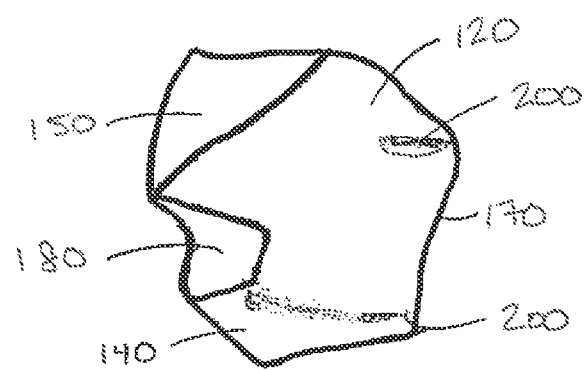
FIG. 4 is an perspective side view of an outside surface of a sealing interface having pleats in accordance with certain embodiments of the present invention.

Referring to FIGS. 2, 3, and 4 the interface portion 120 is created from what is originally a flat piece of material cut to a particular shape S as illustrated in FIG. 2. The interface portion 120 has a maxilla portion 140 having edge B and a hood portion 150 having edge A. To form the interface portion 120, edges A and B are drawn together and attached. When the edges are pulled together, the hood portion 150 and the maxilla portion bow outward and a nose hole 180 is created. In other words, the originally flat material is forced into a non-planar configuration, which creates the three-dimensional shape illustrated in FIGS. 3 and 4. In certain embodiments edges A and B are sewn together, although other methods of attaching the edges such as welding, gluing, or bonding can be employed, as is known to those of skill in the art.

Referring to FIG. 3, in certain embodiments, scribe marks 160 are placed on an outer edge E in pairs. To create the pleats 200 shown in FIG. 4, the material at a first scribe 161 is folded or pleated toward the maxilla portion 140 until it touches the second scribe 162 whereupon it is attached in any manner known in the art and the pleat 200 is created. This process is continued for all of the scribe marks on the edge E of the interface portion 120. In FIG. 3, then, four sets of scribe marks 160 would end up creating four pleats 200. In certain embodiments, all pleats 200 are created by folding the material of the interface portion 120 from top to bottom or in a direction defined as from the hood portion 150 toward the maxilla portion 140. In certain embodiments, the scribe marks 160 for each pleat 200 are 0.5 inches apart and are placed at or near the corners of the interface portion 120.

The material being used for the mask portion 130 is an inelastic cloth material. As used herein, the term cloth is meant to include natural and synthetic fiber cloth, treated cloth, laminates having a cloth base and cloth that is permeable or impermeable to air. In certain embodiments, the nasal interface, by contrast, is constructed of an elastic moisture-vapor breathable material, such as Sympatex®, having the following elastic characteristics:

| White Sympatex Material | | | |
| --- | --- | --- | --- |
| Sample | Initial (in) | Final (in) | % Elongation |
| 1 | 2.08 | 4.71 | 126.4 |
| 2 | 2.08 | 4.73 | 127.4 |
| 3 | 2.09 | 4.74 | 126.8 |
| 4 | 2.08 | 4.67 | 124.5 |
| 5 | 2.10 | 4.78 | 127.6 |
| | | Ave | 126.6 |

This data resulted from the application of a two pound tensile elongation force. All samples were 0.75 inches wide. Sympatex is a registered trademark of Sympatex Technologies GmbH of Germany.

Once the interface portion 120 has been constructed, the edge E is lined up with an edge of the mask portion 130 and attached. In certain embodiments, the interface portion 120 is sewn to the mask portion 130. In use, air at a therapeutic pressure is delivered to the main body 130 via an air tube 132 as illustrated in FIG. 1. The air then inflates the mask portion 130 and the interface portion 120. Due to the structure of the interface portion 120, including the fact that it has pleats 200, the interface portion 120 assumes a three-dimensional pillow shape when inflated. This shape has been found to provide additional surface area contact with user's face and correspondingly provides a better seal for more facial shapes than previous seals were able to provide.

Figure 5:
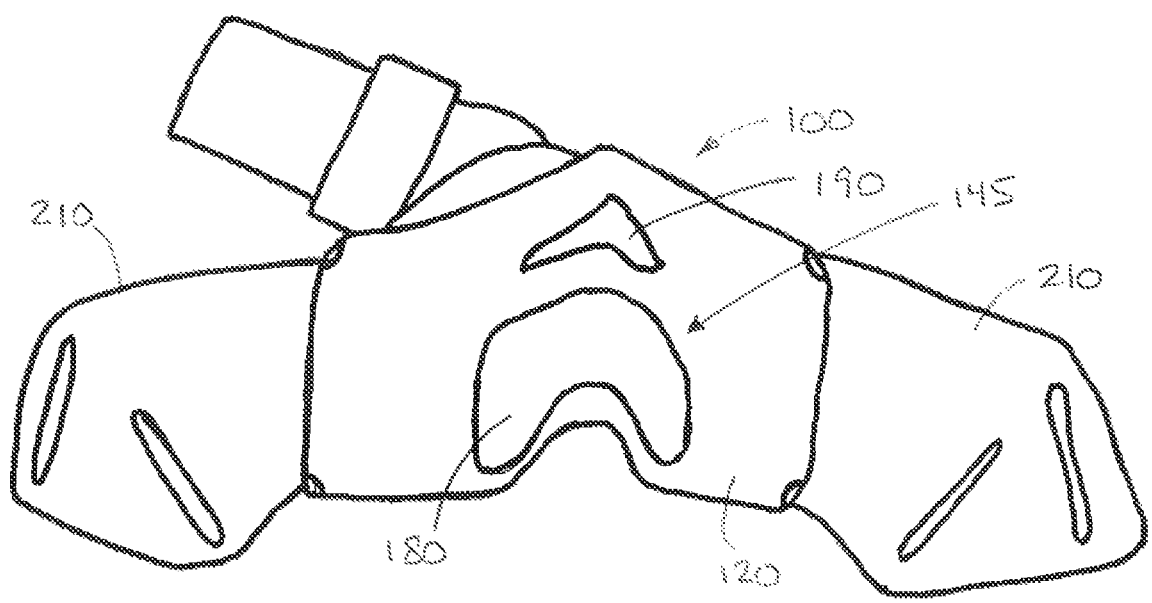
FIG. 5 is an elevational rear view of an inside surface of a sealing interface of the present invention attached to a CPAP mask.

FIG. 5 illustrates the inside surface of a mask assembly 100 constructed in accordance with the present invention. In operation, the interface portion 120 is placed on a user's face with the tip of the user's nose inserted into the nose hole 180. The nose hole 180 being formed in the interface portion 120 and a nose hole rim 145 immediately adjacent the nose hole. Headgear wings 210 are attached to headgear (not shown) that retains the mask on the user's face. In certain embodiments, a structural assistance member 190 is attached to the interface portion 120 for the purpose of adding localized structure and reducing the amount of pillowing in the interface as a result of the supplied air. In some embodiments, the structural assistance member 190 has a chevron shape that is attached in an area corresponding to the bridge of the user's nose. In certain other embodiments, the structural assistance member 190 is attached to the entire nose hole rim 145. In still other embodiments, the structural assistance member 190 has a rectangular shape and is horizontally arranged above the nose hole 180 in an area corresponding to the bridge of the user's nose. In embodiments, the member is constructed of Fabrifoam®, while in other embodiments, it is constructed of a thin aluminum or deformable plastic that can be molded or bent by the user to better fit the user's nose. If constructed of aluminum or plastic, the member 190 may optionally be encased in Fabrifoam® or some similar material as will be known to those of skill in the art. Fabrifoam® is a registered trademark of Applied Technology International, Ltd. of Exton, Pa.

While various illustrative embodiments incorporating the principles of the present teachings have been disclosed, the present teachings are not limited to the disclosed embodiments. Instead, this application is intended to cover any variations, uses, or adaptations of the present teachings and use its general principles. Further, this application is intended to cover such departures from the present disclosure as come within known or customary practice in the art to which these teachings pertain.

We claim:

1. A mask assembly for delivering air at a therapeutic pressure from an air tube to a patient's air passages, the mask assembly comprising:
 a cloth mask portion having a proximal end and a distal end, the distal end removably attached to the air tube for receiving the air from the air tube;
 an elastic interface portion disposed on the proximal end of the flexible cloth mask portion;
 wherein the elastic interface portion has an outer edge, the outer edge being disposed on the proximal end of the cloth mask portion using one of sewing, welding, gluing, and bonding, and the elastic interface portion further comprises one or more pleats in the outer edge; and
 wherein the elastic interface portion is configured to be inflated and expanded by the air at the therapeutic pressure to sealingly deliver the air to the patient's air passages.

2. The mask assembly of claim 1, wherein the cloth mask portion is constructed of an inelastic material.

3. The mask assembly of claim 1, wherein the elastic interface portion is constructed from a single piece of material.

4. The mask assembly of claim 1, wherein the elastic interface portion is constructed from material is stretchable by over one hundred percent.

5. The mask assembly of claim 1, wherein the elastic interface portion is created from material cut into a shape having a first edge and a second edge distal to the first edge, the first edge fixably disposed on the second edge, whereby the elastic interface portion is a three-dimensional structure.

6. The mask assembly of claim 1, wherein the elastic interface portion further comprises a nose hole for receiving the patient's nose, the elastic interface portion configured to expand and seal against the patient's face around the nose upon inflation.

7. The mask assembly of claim 6, further comprising a nose hole rim around the nose hole and a structural assistance member disposed about the rim.

8. The mask assembly of claim 7, wherein the structural assistance member is constructed of a material that is stiffer than the material of which the elastic interface portion is made, whereby the structural assistance member improves the seal around the patient's nose.

9. The mask assembly of claim 1, wherein the elastic interface portion further comprises a structural assistance member for assisting with sealing the elastic interface portion to the user's face.

10. The mask assembly of claim 8, wherein the structural assistance member is shaped substantially like one of a chevron, a rectangle, a triangle, and an arc.

11. The mask assembly of claim 8, wherein the structural assistance member is disposed on the elastic interface portion above the nose hole.

12. The mask assembly of claim 9, wherein the structural assistance member is constructed of a material that is stiffer than the material of which the elastic interface portion is made, whereby the structural assistance member improves the seal around the patient's nose.

13. The mask assembly of claim 11, wherein the structural assistance member is comprised of one of thin aluminum and deformable plastic.

14. The mask assembly of claim 1, further comprising headgear wings and headgear for keeping the mask assembly in position on the patient's face.

\* \* \* \* \*